United States Patent [19]

Kuhn et al.

[11] 4,341,519
[45] Jul. 27, 1982

[54] DENTAL ANGLED VIBRATION MEMBER

[75] Inventors: Bernhard Kuhn, Biberach; Eugen Bochtler, Mittelbiberach, both of Fed. Rep. of Germany

[73] Assignee: Kaltenbach & Voight GmbH & Co., Biberach an der Riss, Fed. Rep. of Germany

[21] Appl. No.: 238,664

[22] Filed: Feb. 26, 1981

[30] Foreign Application Priority Data

Mar. 4, 1980 [DE] Fed. Rep. of Germany ....... 3008297

[51] Int. Cl.³ .............................................. A61C 3/08
[52] U.S. Cl. .................................... 433/122; 433/121
[58] Field of Search ................................ 433/121, 122

[56] References Cited

U.S. PATENT DOCUMENTS 1,641,031 8/1927 Gillard .................................. 433/121
3,967,380 7/1976 Malata ................................. 433/122

FOREIGN PATENT DOCUMENTS 291667 6/1953 Switzerland ........................ 433/122

Primary Examiner—Robert Peshock
Attorney, Agent, or Firm—Scully, Scott, Murphy & Presser

[57] ABSTRACT

A surgical dental or dental technician's angled vibration member consisting of a gripping sleeve portion having a drive shaft supported therein, and an end or head sleeve portion which is arranged at one end of the gripping sleeve portion, whose axis extends at an angle to the axis of the gripping sleeve portion and within which an impact piston is axially reciprocable for a return stroke through the intermediary of an eccentric located on the end of the drive shaft. The impact piston, for the engagement of the eccentric, includes a side recess with a stop, which is provided along its edge and wherein, after passing beyond the stop, has associated therewith an operating spring for effecting the operating stroke, the spring being stressed prior to reaching the stop whereby the impact piston will during its operating stroke impart an impact to an axially movably supported tamping-type vibration tool located at the end inserted in the interior of the head sleeve portion.

16 Claims, 7 Drawing Figures

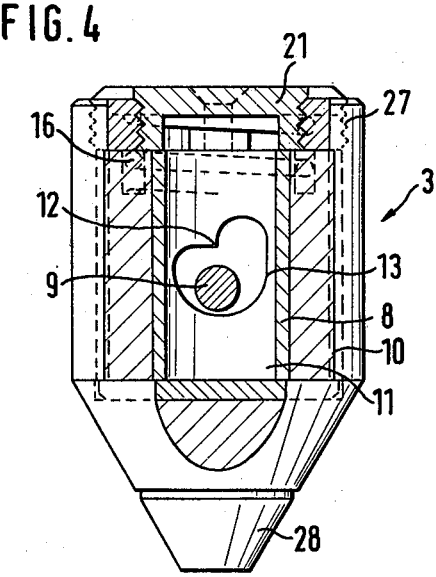
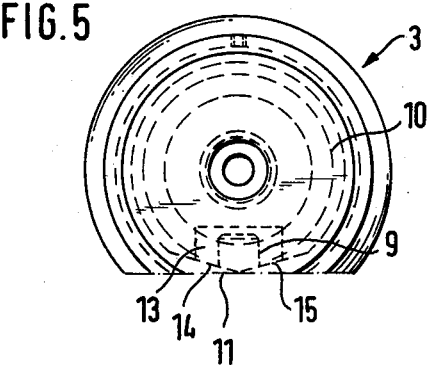

DENTAL ANGLED VIBRATION MEMBER

BACKGROUND OF THE INVENTION

1. Field of the Invention

The present invention relates to a surgical dental or dental technician's angled vibration member consisting of a gripping sleeve portion having a drive shaft supported therein, and an end or head sleeve portion which is arranged at one end of the gripping sleeve portion, whose axis extends at an angle to the axis of the gripping sleeve portion and within which an impact piston is axially reciprocable for a return stroke through the intermediary of an eccentric located on the end of the drive shaft. The impact piston, for the engagement of the eccentric, includes a side recess with a stop, which is provided along its edge and wherein, after passing beyond the stop, has associated therewith an operating spring for effecting the operating stroke, the spring being stressed prior to reaching the stop whereby the impact piston will during its operating stroke impart an impact to an axially movably supported tamping-type vibration tool located at the end inserted in the interior of the head sleeve portion.

The tamping-type vibration tool, for instance, a chisel, will as a result carry out hammering or impacting movements. Such angled members are employed, for example, as riveting hammers during dental riveting procedures, such as amalgam vibrators on compacting tooth fillings, in orthodontics for expanding or adjustment, for example, the bands tooth adjusting arrangements, and so forth. In such an angled member the impacting or operating stroke of the tamping-type vibration work tool is effected through the stressed operating spring and the return stroke under the restressing of the operating spring through the drive shaft by means of the eccentric, with the shaft rotating, for example, at a rotational speed of 100 to 500 rotations per minute.

2. Discussion of the Prior Art

An angled vibration member of that type has become known from U.S. Pat. No. 1,641,031. In this known angled member, the vibration work tool, inclusive of the widened headpiece threaded together therewith and which assumes the impacts of the impact piston, can be pushed through axial pressing of the vibration work tool against the tooth or the like into the interior of the head sleeve portion. Achieved hereby is that the headpiece, and thereby also the work tool, will raise away from the unwidened base of the head sleeve portion which includes a through-aperture, and upon impacting of the impact piston against the headpiece will traverse an impact movement, until the widening of the headpiece for the generation or increase of the impacting or vibration effect of the struck work tool contacts from interiorly against the base of the head sleeve portion. However, encountered thereby is the disadvantage that it is almost impossible after each operating stroke to maintain the work tool inwarldy pressed at the same or desired measure, so that the effected impacts which also act on the gripping sleeve portion of the angled members are extremely irregular, which leads to annoyances of the dentist or dental technician holding the angled members. Through the mentioned irregularity of the impacts there is also afforded the danger that connections of the angled member, for instance, a screw connection will loosen between the head sleeve portion and the gripping sleeve portion.

SUMMARY OF THE INVENTION

Accordingly, it is an object of the present invention to provide a surgical dental or dental technician's angled vibration member of the above-mentioned type in which there is afforded protection for the annoyance-free holding of the angled member during the pressing of the work tool against the tooth or the like and in which, while maintaining a large impact force or vibration effect of the work tool, the axial position of the work tool is adjusted in a defined mode, and thus the work tool can be held constant inwardly pressed to the same or currently desired measure.

The advantages which are achieved by the invention can be ascertained essentially in that the retaining spring which acts on the work tool and facing within the head sleeve portion produces a counterforce to the pressing force exerted by the dentist or the dental technician, which renders it possible that the work tool can be pressed inwardly with a precisely definable or determinable force against a tooth or the like. This pressing force can, due to the retaining spring, also be easily varied in correlation with different surgical dental or dental technical procedures. In each instance, the defined pressing of the work tool which is rendered possible by the retaining spring achieves a uniformity of the work tool impacts whereby there are avoided annoyances to the dentist or dental technician holding the angled member through the gripping of the gripping sleeve portion.

BRIEF DESCRIPTION OF THE DRAWINGS

Reference may now be had to the following detailed description of exemplary embodiments of the invention, taken in conjunction with the accompanying drawings, in which:

FIG. 4 is a sectional view taken along line IV-IV in FIG. 3;

FIG. 5 is a top plan view of a fragmentary segment of the head sleeve portion of FIG. 4;

DETAILED DESCRIPTION

Figure 1:
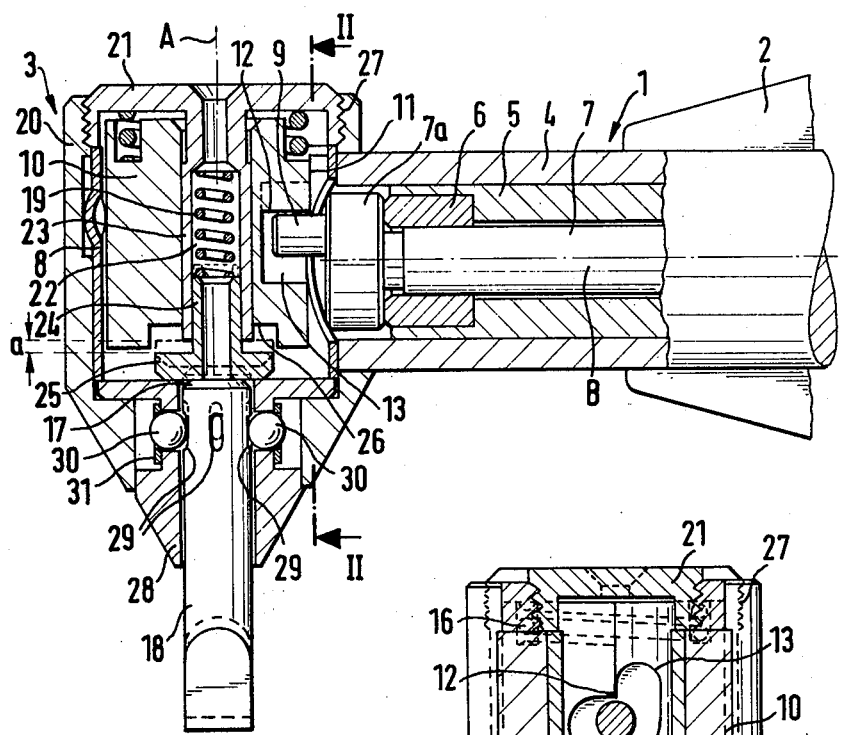
FIG. 1 illustrates, in a partial section, the head sleeve portion and a fragment of the gripping sleeve portion of the angled vibration member with the work tool in the raised position of the impact piston, and in phantom lines the work tool including the hammer piston in the uppermost position.
Figure 2:
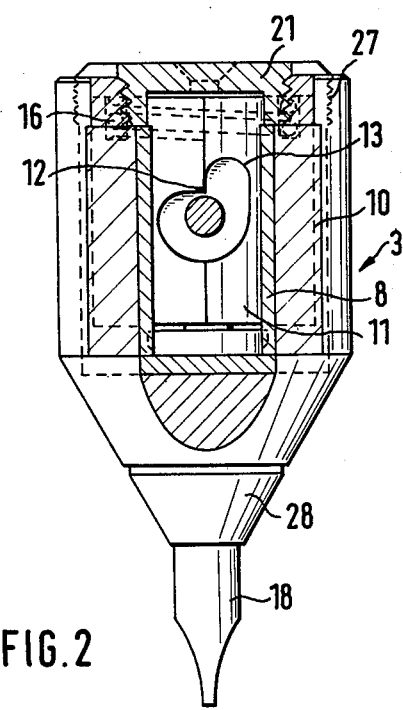
FIG. 2 is a sectional view taken along line II—II in FIG. 1.
Figure 3:
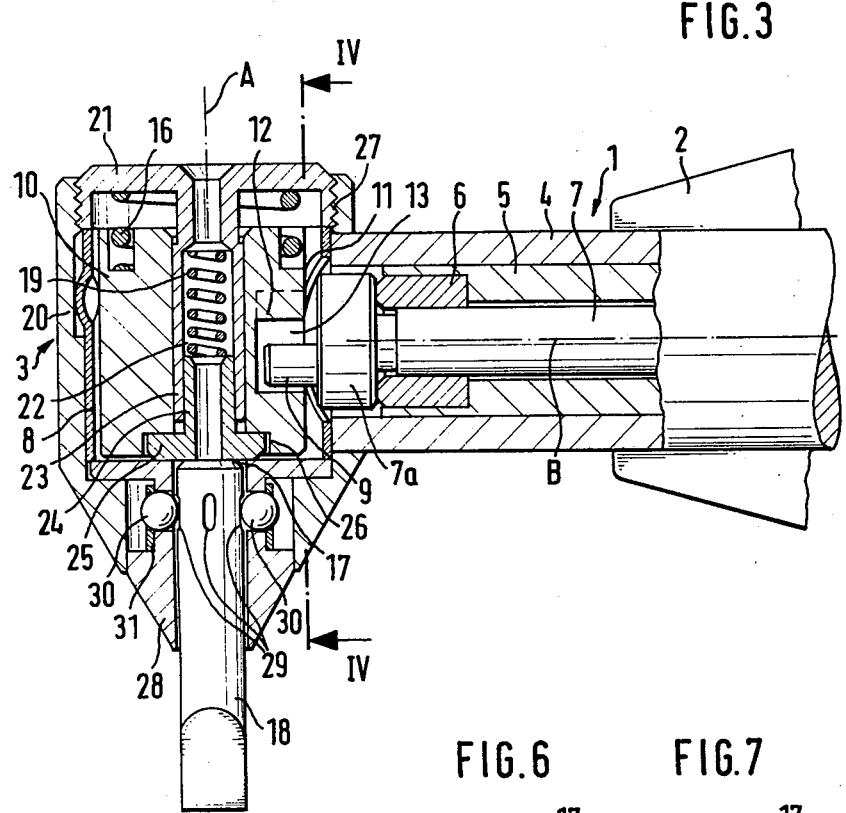
FIG. 3 illustrates the angled vibration member according to FIG. 1 after the operating stroke of the impact piston.

The surgical dental or dental technician's angled vibration member consists of an elongate gripping sleeve portion 1. The actual gripping sleeve is designated by reference numeral 2. Projecting from the gripping sleeve 2 is a tubular shaft 4 within which there is arranged an inner sleeve 5. Within the inner sleeve 5 a draft shaft 7 is rotatably supported by means of a friction bearing 6. The angled vibration member further consists of a head sleeve portion 3 arranged at one end of the gripping sleeve portion whose axis A extends at an angle to the axis B of the gripping sleeve portion 1;

in the case of FIGS. 1 and 3 extending at a right angle. Within the essentially cylindrical head sleeve portion 3 there is arranged a bearing sleeve 8 in which an impact piston 10 is supported for reciprocating axial movement, and subjected to a return stroke by an eccentric 9 located on the widened drive shaft end 7a. The otherwise cylindrical impact piston 10 possesses a side flat 11 (FIG. 5) which at its edge includes a recess 13 having a contact stop 12 for the engagement of the eccentric 9.

As ascertained from FIG. 5 the flat 11 is peaked slightly roof-shaped, wherein the two roof surfaces are designated by reference numerals 14 and 15.

The impact piston 10 has an operating spring 16 associated therewith which, after the eccentric 9 has passed the contact stop 12 of the recess 13, causes the operating or impacting stroke of the impact piston 10 and, while the eccentric 9 approaches the stop 12, the spring is stressed. During its operating or impact stroke the impact piston 10 imparts an impact to the blunt end 17 of an axially movably supported tamping-type vibration work tool 18 extending into the interior of the head sleeve portion 3 and inserted into the latter.

Within the head sleeve portion 3 there is arranged a retaining spring 19 which acts upon the work tool end 17 arranged in the interior of the sleeve portion 3.

The retaining spring 19 which is constructed as a spiral compression pressure spring can be supported against the bearing sleeve 8 of the head sleeve portion 3. Pursuant to FIGS. 1 and 3, the retaining spring 19 is supported against the wall 20 of the head sleeve portion 3 and, in essence, on the cover 21 which can be screwed out of the sleeve.

The retaining spring 19 traverses the impact piston 10. For this purpose, the impact piston 10 is provided with a through-aperture 22 for the passage of the retaining spring 19 which is supported against the cover 21. The through-aperture 22 is in the form of a central break-through extending axially through the impact piston 10, in which there is provided a receiving sleeve 23 which receives the retaining spring 19 and which is fixedly connected with the head sleeve end portion 3 and, in effect, with the cover 21 with the last-mentioned sleeve, and which concurrently serves as a guide for the impact piston 10.

For intensifying the impacting effect of the impact piston 10, intermediate the retaining spring 19 and the vibration work tool 18 there is arranged a hammer piston 24 which, at the end facing towards the vibration tool 18, includes an annular flange-shaped widening 25 which is engageable into a corresponding annularly-shaped depression 26 at the lower end, in effect, on the impacting end surface of the impact piston 10.

The dimensions are so selected that the receiving sleeve 23, at an unstressed retaining spring 19, ends at a distance 'a' ahead of the annular flange-shaped widening 25 of the hammer piston 24, as shown in FIG. 1. In order to vary this distance 'a', the cover 21, as previously mentioned, is screwed together with the head sleeve portion 30 and, in essence, by means of the screw thread 27.

The vibration work tool 18 is axially movably supported within a guide sleeve 28 forming the end of the head sleeve portion towards the work tool. For limiting this axial movement the vibration work tool 18 possess along the circumferential surface of the work tool shaft pursuant to FIGS. 1, 3 and 6, four circumferentially equally spaced latching grooves 29 in the form of axial slots, whose axial expansion corresponds to the length of the axial path of movement of the vibration work tool 18. Each of these four latching grooves 29 has a locking member 30 associated therewith each formed by a locking ball standing in engagement with the associated latching groove 29 under the effect of a spring 31. Through the exertion of a pull on the free work tool end, or of pressure by means of a pressure pin through the central cover and hammer piston opening against the inner end of the work tool shaft, the vibration work tool 18 can be pulled out of or removed from the guide sleeve 28 by overcoming the spring force.

Figures 6, 7:
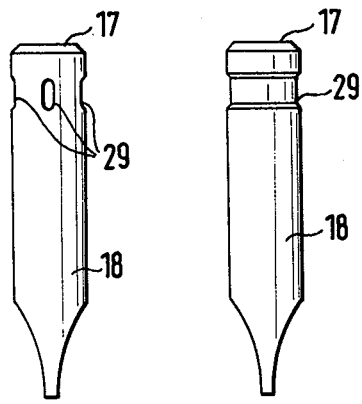
FIG. 6 is a side elevational view of a vibration work tool.
FIG. 7 is a modified embodiment of a vibration work tool in comparison with that of FIG. 6.

In lieu of four individual latching grooves 29 which are formed as axial slots, pursuant to FIG. 7 there can also be provided a single latching groove 29 which is formed by an annularly shaped radial groove extending about the circumference of the work tool shaft. In this instance, it is possible to provide one or also a plurality of locking members 30.

When during the rotation of the drive shaft 7 the angle member is pressed with the free end of the vibration work tool 18 against a tooth or the like, then the end of the vibration work tool projecting into the interior of the head sleeve portion 3 is pushed inwardly counter to the effect of the retaining spring 19 so that upon stressing of the support spring 19, there reduces the distance 'a'. Herewith the surface of the widening 25 the hammer piston 24 approaches the lower annular end surface of the receiving sleeve 23 so that, during the impacting stroke of the impact piston 10, the impacting path and, resultingly, the impact force of the hammer piston 24 will increase and the effect of the vibration work tool 18 will intensify. Due to the retaining spring 19, the dentist or the dental technician can thus hold the angle member with the desired and precisely defined pressing force in contact against a tooth or the like.

What is claimed is:

1. In a surgical dental or dental technician's angled vibration member; including a gripping sleeve portion having a drive shaft supported therein; a head sleeve portion arranged at one end of said gripping sleeve portion and having an axis extending at an angle to the axis of the gripping sleeve portion; an impact piston axially reciprocable in said head sleeve portion; an eccentric at the drive shaft end for imparting a return stroke to said impact piston; said impact piston having at its edge a side recess with a contact stop for the engagement of said eccentric; and having an operating spring associated therewith for effecting the operating stroke after passing of the contact stop, said spring being stressed prior to reaching the contact stop, so that the impact piston during its operating stroke will impart to the end of the axially movably supported, tamping-type vibration work tool in the interior of the head sleeve portion; the improvement comprising: a retaining spring in said head sleeve portion acting on the end of the vibration work tool at the interior of the head sleeve portion, said retaining spring being supported on the head sleeve portion; and a hammer piston being arranged intermediate said retaining spring and the vibration work tool.

2. Angle member as claimed in claim 1, said retaining spring being supported against a cover of said head sleeve portion.

3. Angle member as claimed in claim 1, said retaining spring comprising a compression spring.

4. Angle member as claimed in claim 3, said compression spring being a helical coil spring.

5. Angle member as claimed in claim 1 or 4, said impact piston including an aperture for the arrangement of the retaining spring supported on the head sleeve portion.

6. Angle member as claimed in claim 5, said through aperture having the shape of a central, axially extending opening in said impact piston.

7. Angle member as claimed in claim 6, comprising a receiving sleeve for said retaining spring being arranged in said opening.

8. Angle member as claimed in claim 7, said receiving sleeve being fixedly interconnected with said head sleeve portion.

9. Angle member as claimed in claim 8, said receiving sleeve being fixed interconnected with the cover of said head sleeve portion.

10. Angle member as claimed in claim 7, said receiving sleeve forming a guide means for said impact piston.

11. Angle member as claimed in claim 1, comprising an annular flange-shaped widening on the end of said hammer piston facing towards the vibration work tool; and a complementary annular recess being arranged in the impact end surface of said impact piston adapted to be engaged by said annular widening.

12. Angle member as claimed in claim 11, said receiving sleeve ending at a predetermined distance ahead of the annular flange-shaped widening of the hammer piston at an unstressed retaining spring.

13. Angle member as claimed in claim 12, comprising threaded screw means connecting said cover with the head sleeve portion for varying said distance.

14. Angle member as claimed in claim 1, comprising a guide sleeve for the vibration work tool forming the work tool end of said head sleeve portion, including at least one latching groove for the axial movement of said sleeve along the circumferential surface of the work tool shaft and conforming in the axial extension thereof to the length of the axial path of movement of the vibration work tool; at least one locking member being supported in said guide sleeve; and spring means acting on said locking member to bias the latter into engagement with said latching groove; said locking member comprising a locking ball.

15. Angle member as claimed in claim 14, said latching groove comprising a ring-shaped radial groove extending about the circumference of the work tool shaft.

16. Angle member as claimed in claim 14, comprising a plurality of said latching grooves being formed by axial grooves arranged at a circumferential spacing from each other.

* * * * *